(12) United States Patent
Lai

(10) Patent No.: US 10,724,979 B2
(45) Date of Patent: Jul. 28, 2020

(54) GAS SENSOR ELEMENT

(71) Applicant: NITTO DENKO CORPORATION, Osaka (JP)

(72) Inventor: Qianxi Lai, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 15 days.

(21) Appl. No.: 15/576,155

(22) PCT Filed: May 25, 2016

(86) PCT No.: PCT/US2016/034191
§ 371 (c)(1),
(2) Date: Nov. 21, 2017

(87) PCT Pub. No.: WO2016/191501
PCT Pub. Date: Dec. 1, 2016

(65) Prior Publication Data
US 2018/0136156 A1 May 17, 2018

Related U.S. Application Data

(60) Provisional application No. 62/166,236, filed on May 26, 2015.

(51) Int. Cl.
*G01N 27/12* (2006.01)
*G01N 33/497* (2006.01)

(52) U.S. Cl.
CPC ......... *G01N 27/125* (2013.01); *G01N 33/497* (2013.01)

(58) Field of Classification Search
CPC ............................ G01N 27/125; G01N 33/497
USPC ....................................................... 73/23.3
See application file for complete search history.

(56) References Cited

U.S. PATENT DOCUMENTS

| 6,171,389 | B1* | 1/2001 | Anderson | C30B 11/04 117/2 |
| 9,643,186 | B1* | 5/2017 | Ahmad | G01N 33/98 |
| 2008/0221806 | A1* | 9/2008 | Bryant | G01N 27/127 702/22 |
| 2013/0064747 | A1* | 3/2013 | Zhou | B01D 53/228 423/230 |

(Continued)

FOREIGN PATENT DOCUMENTS

JP 2001318069 A 11/2001

OTHER PUBLICATIONS

International Search Report for PCT/JP2016/034191, dated Aug. 5, 2016.

(Continued)

*Primary Examiner* — Nimeshkumar D Patel
*Assistant Examiner* — Jean F Morello
(74) *Attorney, Agent, or Firm* — K&L Gates LLP; Louis C. Cullman; Hal Gibson

(57) ABSTRACT

Gas sensors are described herein that are useful for selectively detecting a second gas (e.g. isoprene) in the presence of a first gas (e.g. acetone). The gas sensors include a sensor element which includes a semiconductor sensing material and a porous material. The sensor element is configured so that the porous material absorbs more of the first gas than the second gas. Thus, when the gas being analyzed, such as a mammalian (including human) breath, a greater proportion of the second gas comes into contact with the semiconductor sensing material.

18 Claims, 2 Drawing Sheets

(56) References Cited

U.S. PATENT DOCUMENTS

2014/0015548 A1* 1/2014 Naughton ............... G01R 27/26
                                                     324/658
2015/0346190 A1   12/2015 Sambandan
2015/0353446 A1* 12/2015 Feyen ..................... B01J 29/48
                                                     585/417
2016/0084786 A1*  3/2016 Suzuki ................... G01N 27/16
                                                     73/31.06

OTHER PUBLICATIONS

Ayo Afonja et al., Gas Sensing Properties of Composite Tungsten Trioxide-Zeolite Thick Films, ECS Transactions 77 (Jan. 1, 2009).

Russell Binions et al., Discrimination Effects in Zeolite Modified Metal Oxide Semiconductor Gas Sensors, 11(5) IEEE Sensors 1145 (Oct. 7, 2010).

M Vilaseca et al., Development and application of micromachined Pd/SnO2 gas sensors with zeolite coatings, 133(2) Sensors & Actuators B 435 (Aug. 12, 2008).

Xiaowen Xu et al., Zeolite-based Materials for Gas Sensors, 6(12) Sensors 1751 (Dec. 13, 2006).

Yangong Zheng et al., Exploitation of Unique Properties of Zeolites in the Development of Gas Sensors, 12(12) Sensors 5170 (Apr. 20, 2012).

* cited by examiner

GAS SENSOR ELEMENT

CROSS REFERENCE TO RELATED APPLICATIONS

This application is the U.S. national phase of PCT Application No. PCT/JP2016/034191, filed May 25, 2016, which claims the benefit of U.S. Provisional Application No. 62/166,236, filed May 26, 2015. The contents of each of these applications are hereby incorporated herein in their entirety.

BACKGROUND

Field

Some embodiments are related to medical devices, and also related to oxide compositions for qualitative or quantitative analysis of breath components.

Description of the Related Art

Certain illnesses and physical conditions can be associated with the presence of certain gases in mammalian expiratory breaths. Among the most abundant VOCs in human breath are ethanol, acetone, and isoprene. Acetone is a biomarker of fat burning and isoprene is a biomarker of cholesterol synthesis in human body. Thus, there is a need for an isoprene sensor which can detect low concentration such as in mammalian expiratory breaths for use in portable devices that could be used for diagnosis and self-monitoring of outpatients having various physical conditions.

SUMMARY

Some embodiments include a sensor element comprising: a semiconductor sensing material having an electroconductivity that is sensitive to the presence of a first gas and a second gas; and a porous material containing pores having a pore diameter larger than the kinetic diameter of the first gas and smaller than 1.5 times the kinetic diameter of the second gas; wherein the sensor element is configured so that the porous material adsorbs more of the first gas than of the second gas so that detection of the second gas by the sensor element is more sensitive as compared to detection of the first gas by the sensor element. Some embodiments include a gas sensor comprising this sensor element. Some embodiments include an isoprene sensor comprising this sensor element.

Some embodiments include a breath analyzing device comprising a container configured for reception of mammalian breath, and a sensor element described herein disposed within the container and in physical contact with gas inside the container.

Some embodiments include a medical diagnosis system comprising a gas sensor or a breath analyzing device described herein and a portion of a breath exhaled by a mammal.

Some embodiments include a method of determining levels of a gas, such as isoprene levels, in mammalian breath comprising exposing the isoprene sensor of claim 18 to a breath of a mammal.

These and other embodiments are described in greater detail below.

DETAILED DESCRIPTION

Figure 1:
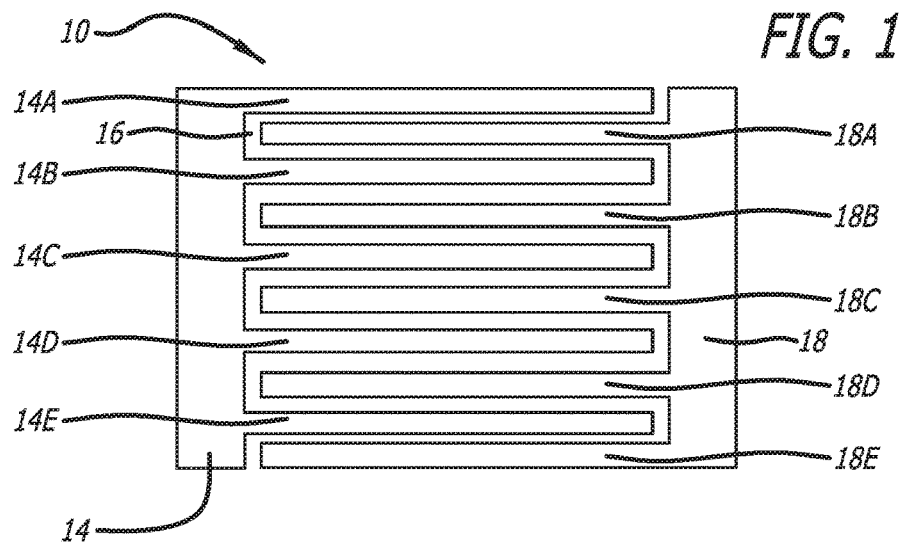
FIG. 1 is a plan view of some embodiments of a device described herein.

Generally, the gas sensors described herein may be used to selectively detect one gas over another. For example, they may be useful in detecting isoprene over other gases such as acetone. Thus, a gas sensor may be an isoprene sensor.

One important use for these gas sensors, such as a selective isoprene sensor, is to determine gas levels, such as isoprene levels, in mammalian breath, such as human breath. For example, a gas sensor could be exposed to a breath of a mammal, e.g. by having the mammal (such as a person) blow over, onto, or into the gas sensor.

In particular, the gas sensors described herein are useful for selectively detecting a second gas (e.g. isoprene) in the presence of a first gas (e.g. acetone). However, a gas sensor could also detect any of isoprene, acetone, ethanol, as the second gas, in the presence of any of the others as the first gas.

The sensor element, which could be used in a variety of gas sensor devices, includes a semiconductor sensing material and a porous material. The sensor element is configured so that the porous material absorbs more of the first gas than the second gas. Thus, when the gas being analyzed, such as a mammalian (including human) breath, a greater proportion of the second gas comes into contact with the semiconductor sensing material. As a result, the sensor element is more sensitive to the second gas as compared to the first gas.

The porous material is particularly useful when the semiconductor has an electroconductivity that is sensitive to both the first gas and the second gas. Thus, without the porous material, it may be difficult for the amount of the second gas to be accurately determined because of the presence of the first gas. The porous material can reduce the complication that sensitivity to the first gas causes in determining the amount of the second gas when it is present in a gas mixture that contains the first gas.

A semiconductor sensing material could be any semiconductor that has an electroconductivity that is sensitive to a gas of interest, such as isoprene, acetone, or ethanol. For example, the conductivity or resistivity of the semiconductor could increase or decrease in the presence of the gas to be analyzed.

A semiconductor sensing material could include an n-type semiconductor, which may be polycrystalline. In some embodiments, the n-type semiconductor material can comprise an octahedral lattice, a monoclinic phase material, such as a monoclinic I phase material or a monoclinic II phase material; a triclinic phase material, an orthorhombic phase material, a tetragonal phase material, or a cubic phase material. In some embodiments, the n-type semiconductor material can have a spontaneous dipole moment.

In some embodiments, the n-type semiconductor material can be $WO_3$, including α-phase $WO_3$ (α-$WO_3$), β-phase $WO_3$ (β-$WO_3$), δ-phase $WO_3$ (δ-$WO_3$), ε-phase $WO_3$ (ε-$WO_3$), γ-phase $WO_3$ (γ-$WO_3$), cubic $WO_3$, or a combination thereof. In some embodiments, the $WO_3$ includes, or is γ-WO$_3$. In some embodiments, the n-type semiconductor can be epsilon phase tungsten oxide, gamma phase tungsten oxide, or a mixture thereof. In some embodiments, the WO$_3$ includes, or is ε-WO$_3$. In some embodiments, the WO includes, or is η-WO$_3$.

In some embodiments, the semiconductor can comprise ε-WO$_3$ and a second n-type semiconductor material. For example, ε-WO$_3$ may be at least 55%, at least 60%, at least 65%, at least 70%, 90%, 95%, 99%, by weight or molar percentage, of the n-type semiconductor material. For semiconductors comprising a combination of ε-WO$_3$ and γ-WO$_3$ the ratio of the two phases can be expressed as the ratio of the ε-phase WO$_3$ XRD peak at about 49.34 2 theta to the γ-phase WO$_3$ XRD peak at about 26.44 2 theta. In some embodiments, a spontaneous dipole of the ε-WO$_3$ may be related to the material lattice so that changes in the lattice may change the strength of the dipoles (in other words, a change in the spontaneous polarization). In some embodiments, a change in the spontaneous dipole moment can result in a change in the surface charge of the material.

Comparison of an x-ray diffraction pattern of a given standard and the produced sample is one of a number of methods that may be used to determine whether the sample comprises a particular phase. Exemplary standards include those XRD spectra provided by the National Institute of Standards and Technolgy (NIST) (Gaitherburg, Md., USA) and/or the International Centre for Diffraction Data (ICDD, formerly the Joint Committee on Powder Diffraction Standards [JCPDS]) (Newtown Square, Pa., USA).

In some embodiments, the semiconductor sensing material absorbs visible light. For example, the semiconductor sensing material may have an absorption edge of 600 nm or less.

A semiconductor sensing material may include a semiconductor material, such as an n-type semiconductor material, that is doped or loaded with an additional element. Doped elements include elements that are incorporated into the crystal lattice of the compound, for example as substituted within defined positions within the crystal lattice or otherwise interstitially included within the crystal. Loaded elements include included elements that are non-valently combined, e.g., a physical mixture and/or adjacent disposition of a first material and a second material. Any element that can affect the sensing properties of the semiconductor material may be doped or loaded into the semiconductor material. Examples of useful dopants may include a Group III element, such as B, Al, Ga, In, etc.; Cr; Si; etc. In some embodiments element that is doped or loaded into the semiconductor sensing material can be B, including B, B$^+$, B$^{2+}$, or B$^{3+}$.

Doped elements can be provided as precursors added generally during synthesis. In some embodiments, the dopant can have an ionic diameter of sufficiently small size to increase the stability of the ε-phase WO$_3$. In some embodiments, the dopant can have an ionic diameter of less than about 50 pm (1×10$^{-12}$ meters). In some embodiments, the dopant can have an ionic diameter from about 5 pm, 10 pm, 15 pm, 20 pm, 30 pm, 35 pm, to about 45 pm, to about 50 pm, to about 55 pm. It is believed that doping with a smaller ionic diameter dopant molecule than ε-phase WO$_3$, e.g., about 74 pm, can contract the overall cell volume of the crystal. Examples of ionic diameters for ionic species generally at 90% semiconductor and 10% dopant entities are described in Table 1.

TABLE 1

| Ionic species | Ionic diameter |
| --- | --- |
| W$^{6+}$ | 74 pm |
| Cr$^{6+}$ | 58 pm |
| Si$^{4+}$ | 54 pm |
| B$^{3+}$ | 41 pm |

In some embodiments, a boron dopant, e.g. B, B$^+$, B$^{2+}$, or B$^{3+}$, can be present in the semiconductor material in an amount that is at least about 0.0001%, at least about 0.01%, at least about 0.05%, at least about 0.08%, at least about 0.10%, up to about 0.15%, up to about 0.2%, up to about 0.225%, up to about 0.4%, up to about 0.5%, up to about 0.75%, up to about 1%, up to about 2%, up to about 5%, up to about 10%, about 0.01-10%, or about 0.1-0.3%, by weight or moles of the semiconductor sensing material, or any weight % or mole % in a range bounded by any of these values. In some embodiments, the semiconductor sensing agent contains about 0.225% of B by weight.

A sensor element may include any porous material that contains pore materials of a size that can selectively remove (e.g. adsorb) the first gas in a way that improves relative sensitivity toward the first gas. For example, a porous material may contain pores having diameter larger than the kinetic diameter of the first gas to selectively retain more of the first gas therein. The term "kinetic diameter" has the ordinary meaning known to a person of ordinary skill in the art, and is a reflection of the smallest effective dimension of a given molecule, taking into consideration the kinetic motion of the given molecule and its atomic dimensions.

It is also helpful for the pores to have a pore diameter, or an average pore diameter, that is smaller than about 1.5 times, about 1.2 times, or about 1.35 times the kinetic diameter of the second gas.

Kinetic diameters of some gases of interest are shown in Table 2:

TABLE 2

| Compound | Kinetic diameter |
| --- | --- |
| acetone | 4.5 Å |
| isoprene | 5.5 Å |
| ethanol | 4.5 Å |
| Methane | 3.8 Å |
| H$_2$O | 2.7 Å |

In some embodiments, a porous materials can be a zeolite or metal organic framework material. Examples of suitable zeolites include: large-pore zeolites in which the structural pore openings comprise 12 atoms, such as zeolite X and Y, gumerinite, zeolite β, mordenite, offretite, EMT, SAPO-37, and beryllophosphate X; extra-large-pore zeolites in which the structural pore openings comprise 14 or more atoms, such as cloverite; medium-pore zeolites in which the structural pore openings comprise 10 atoms, such as ZSM-5 (pentasil-zeolite), ferrierite, heulandite, and weinebeneite; and small-pore zeolites in which the structural pore openings comprise 8 or fewer atoms, such as analcime, chabazite, erionite, and zeolite A. In some embodiments, the zeolite materials can be ZSM-5, ZSM-11, Zeolite Y, ZSM-12, β zeolite, or Titano silicalite TS-1. In some embodiments, the zeolite comprises ZSM-5. In some embodiments, the Si/Al ratio of the zeolite materials can be 1-500. The Si/Al ratio determines the acidity and hydrophobicity of the materials and it can in addition determine what molecules the porous material more selectively absorbs and reacts with. The higher the ratio, more hydrophobic and less acidic, thus favors the absorption of less polar molecules such as the hydrocarbons. In some embodiments, the porous material can have a predominantly monoclinic phase.

In some embodiments, the porous material contains pores having a diameter, or an average diameter, that is greater than about 4.5 Å, up to about 8.25 Å, up to about 9 Å, about 4.6-9 Å, about 5.1-5.5 Å, about 5.4-5.6 Å, about 5.5 Å, about 5 Å, about 6 Å, or any diameter in a range bounded by any of these value s.

Exemplary porous materials and their respective pore sizes are described in Table 3:

TABLE 3

| Compound | Pore size |
| --- | --- |
| ZSM-5 | 5.1-5.5 Å |
| ZSM-11 | 5.3-5.4 Å |
| Zeolite Y | 7.4 Å |
| ZSM-12 | 5.6-6.0 Å |
| beta zeolite | 6.6-6.7 Å |
| Titano silicalite TS-1 | 5.6-5.8 Å |

There are a number of ways that pore diameter can be determined, such as by $N_2$ absorption at 77° K.

In some embodiments, the sensor element has a sensitivity ratio of the second gas to the first gas of at least about 1.5, at least about 3, at least about 4, or at least about 5. The "gas sensitivity" can be determined from the ratio of the minimum sensor resistance after exposed to the test gas ($R_{gas}$) to the baseline resistance at ambient environment ($R_{air}$), $S=R_{gas}/B_{air}$.

$WO_3$ compounds, e.g. in nanopowder form, can be prepared by many different methods including thermal plasma (direct current and including radio frequency inductively-coupled plasma (RF-ICP)), solvothermal, solid state reaction, pyrolysis (spray and flame), and combustion. Combustion synthesis methods as described in PCT application entitled "Supported Photocatalyst and method of production," (PCT/US2013/010201), filed Jan. 4, 2014, are useful because the high temperature may aid in doping boron into the tungsten oxide lattice or may contribute to the stabilization of the epsilon phase tungsten oxide. Hence, combustion loading processes are preferred. For example, when preparing $WO_3$ nanopowders, a liquid dispersion of additional additives, e.g., ammonium metatungstate, ammonium nitrate and/or glycine, in water (5-20 wt % solid in water) can be sprayed into the plasma volume using a two-fluid atomizer. Preferably, the precursor can be present to about 20 wt % solid in water. The plasma can be operated at about 25 kW plate power with argon, nitrogen and/or oxygen gases. The particles formed from the condensed vapor from the plasma can then be collected on filters. In some embodiments, the particle surface areas range as measured using BET from about 1 $m^2/g$ to about 500 $m^2/g$, about 15 $m^2/g$ to 30 $m^2/g$, or about 20 $m^2/g$. In some embodiments, the obtained $WO_3$ may be heated from about 200° C. to about 700° C. or about 300° C. to about 500° C.

Some sensor elements may have a structure represented by FIG. 1. In FIG. 1, sensor element 10 can comprise a first electrode 14 and a second electrode 18. For sensors having a structure represented by FIG. 1, a sensing material 16, e.g., an n-type semiconductor material, is disposed between the first and second electrodes. In some embodiments, the n-type semiconductor material can contact or can electrically connect the first and second electrodes. In some embodiments, the n-type semiconductor material can be disposed between and/or physically contacting both the first and second electrodes.

Figure 2:
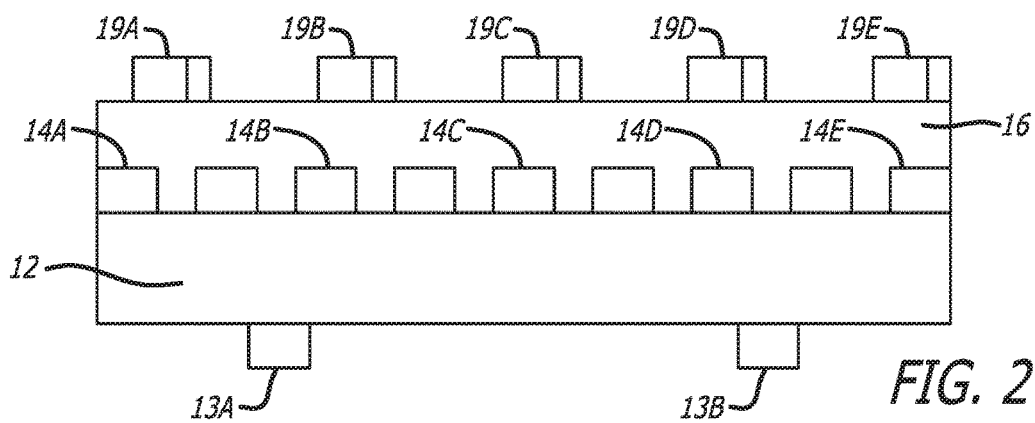
FIG. 2 is an elevational view of an embodiment of a device described herein.

As shown in FIG. 2, the sensor element 10 can comprise a first electrode comprising a plurality of electrode fingers 14A-E disposed over a substrate 12. In some embodiments, the second electrode can also comprise electrode fingers, e.g. Electrode fingers 14A-E and 18A, 18B can be interdigitated as shown. In some embodiments, a heater element 13A, 13B can be disposed proximal to the electrodes. In some embodiments, the interdigitated fingers are sufficiently close to enable closing an electrical circuit across the gap through the semiconducting material. In some embodiments, there can be at least 2, at least 3, at least 4, or at least 5 interdigitated fingers.

The distance between the electrodes, e.g. the first electrode and the second electrode, can be any suitable distance that allows changes in conductivity caused by the presence of analyte gases of interest to be detected, e.g. between 0.01-100 mils, between about 0.1-25 mils, or between about 0.5-10 mils, In some embodiments, a layer of the porous material 19 can be adjacent the plurality of electrode fingers 14A, 14B, 14C and semiconductor material 16. In some embodiments, a layer of the porous material 19 can be contacting the plurality of electrode fingers 14A-14E and semiconductor material 16. In some embodiments, a layer of the porous material or a plurality of porous material portions (19A-E) can be disposed atop semiconductor material 16. In some embodiments, a layer of the porous material covers 20-99%, and/or 30-98%, and/or 40-95%, and/or 50-90% of the surface of sensing material. In some embodiments, the porous material and the sensing material are mixed in one layer.

The first and second electrodes can be formed from a conductive material. In some embodiments, the electrodes can be gold [Au], platinum (Pt), palladium (Pd) and/or any mixtures thereof.

The temperature at which the sensor element functions can be affected by different semiconductor materials, dopants, loadants and/or co-catalysts. In some embodiments, the electrodes 14 and 18 are disposed on a substrate 12. In some embodiments, the n-type semiconductor composition combined with any dopants and/or co-catalysts can be formed into a slurry. The slurry can be drop coated on the electrodes and substrate. In some embodiments, the excess slurry can be removed from the gas sensor element, so that the remaining n-type semiconductor slurry fills the gap between the electrodes, as in FIG. 2.

In some embodiments, the sensor element can detect the presence of constituent gases within a range of temperatures. In some embodiments, the sensor element can detect the presence of constituent gases between about 200-400° C., about 200-220° C., about 220-240° C., about 240-260° C., about 260-280° C., about 280-300° C., about 300-320° C., about 320-340° C., about 340-360° C., about 360-380° C., or about 380-400° C., or any temperature in a range bounded by any of these values. In some embodiments, the sensor element can detect the presence of constituent gases at room temperature.

The sensor element may detect the presence of analyte gases of interest that are present at low concentrations, such as in a range of about 0.0005-5 ppm, about 0.001-10 ppm, about 0.005-2.5 ppm, about 0.01-5 ppm, about 0.05 ppm-0.5 ppm, about 0.1 ppm-1.0 ppm, 0.25 ppm, 0.5 ppm, or any concentration in a range bounded by any of these values.

Figure 3:
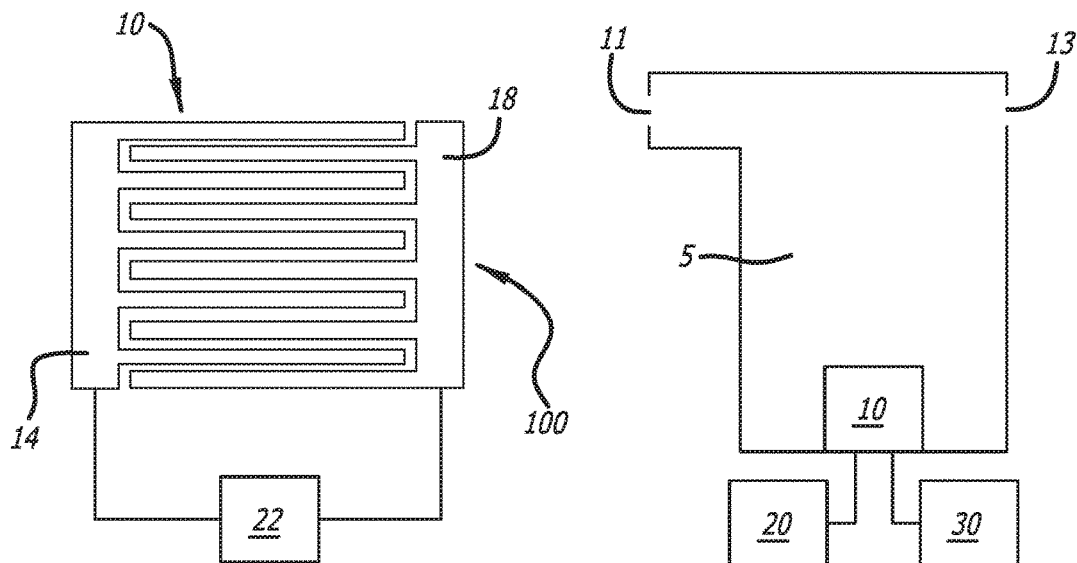
FIG. 3 is an elevational view of an embodiment of a device described herein.

FIG. 3 depicts an embodiment of a sensor system 100. In some embodiments, the first electrode 14 and second electrode 18 of sensor element 10 are electrically connected to a resistivity monitor 22. in some embodiments, the presence of the analyte, e.g., isoprene and acetone, in close proximity to the electrodes and/or semiconductor alters the electroconductivity, or decreases the resistance of the circuit, between the electrodes 14 and 18, providing a change in the measured resistivity of the circuit. In some embodiments, a measurable correlation between the amount of analyte, e.g., isoprene and acetone, present in close proximity to the electrodes and the variation in resistance exhibited by the circuit can be effected. In some embodiments, the change in resistivity can be at least about 152 megaohm per 100 part per million (ppm) of analyte present in the tested sampling. The reading is obtained by measuring absolute resistance value and its change directly using computer controlled multi-meter.

Figure 4:
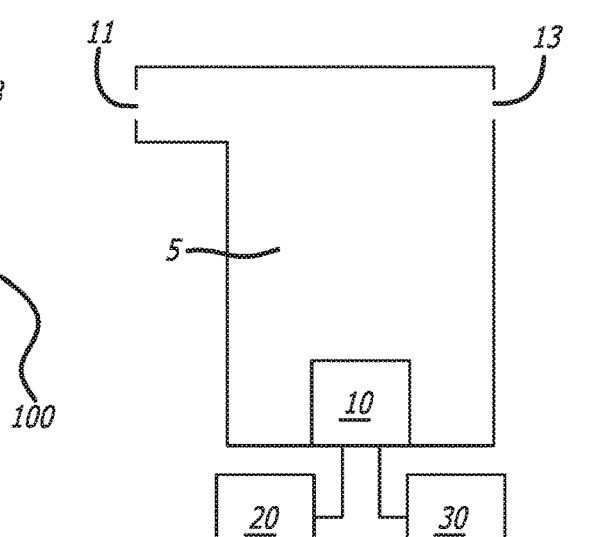
FIG. 4 is a schematic of some embodiments of a device described herein.

FIG. 4 depicts another embodiment of a sensor system for detecting the presence of constituent gases, e.g., isoprene, in a volume of gas. The system may comprise a chamber 5 for containing the volume of gas to be evaluated, and a sensor element 10, disposed therein. In some embodiments, the chamber 5 can comprise a gas inlet 11 for allowing inflow of a gas 9. In some embodiments, the chamber 5 can comprise a gas outlet 13 allowing outflow of gas. In some embodiments, the device can comprise a power supply 20, and a measurement device 30 for analyzing the data received from the gas sensor element.

Figures 5, 6:
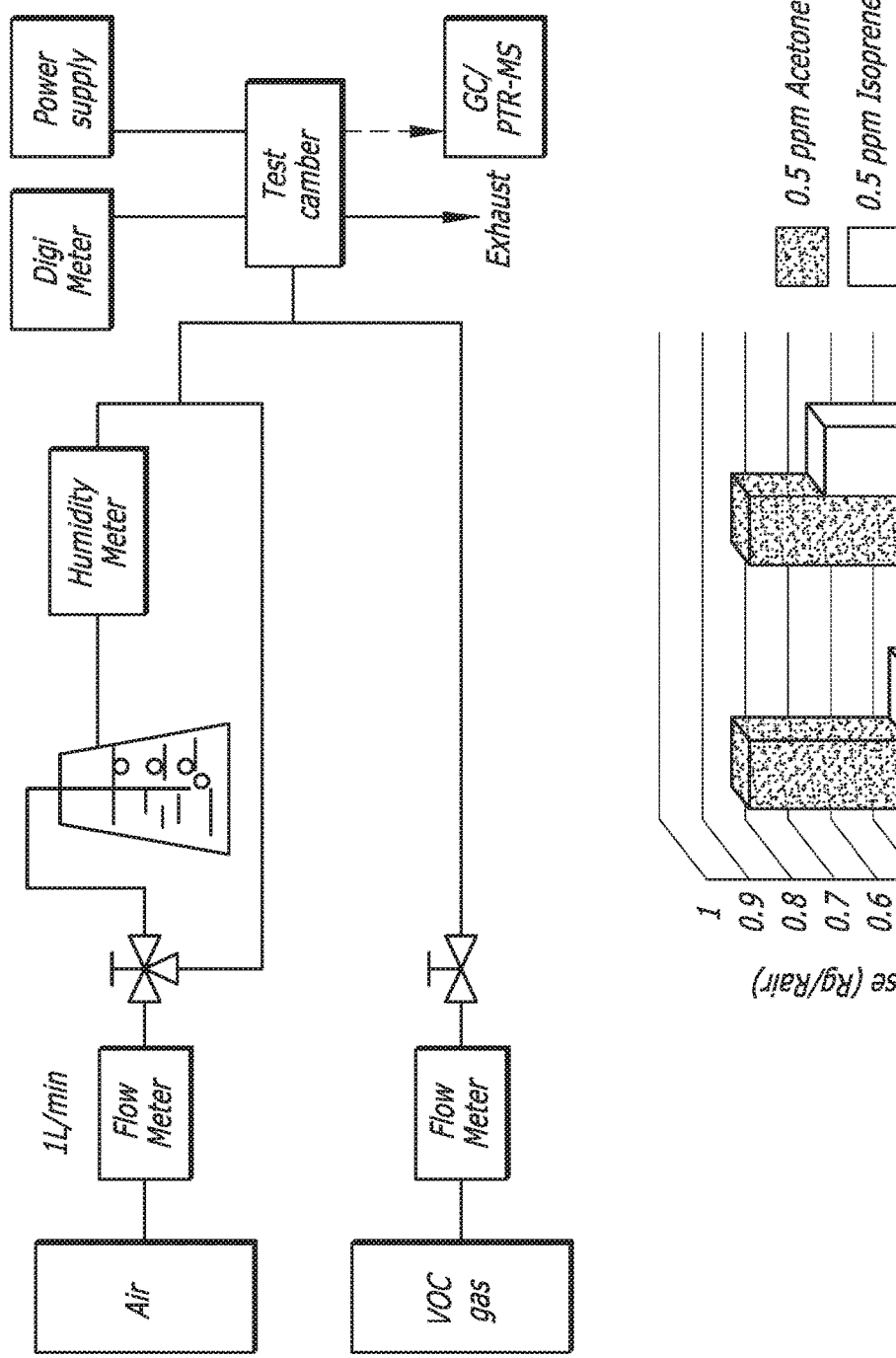
FIG. 5 is a schematic of the testing apparatus used herein.
FIG. 6 is a graph depicting the resistivity response to acetone and isoprene samples of a sensor embodiment as described in the examples

FIG. 5 depicts a schematic of the gas sensor system for detecting the presence of acetone/isoprene in a volume gas as described in the examples.

The following embodiments are contemplated:

Embodiment 1

A sensor element comprising:
- a semiconductor sensing material having an electroconductivity that is sensitive to the presence of a first gas and a second gas; and
- a porous material containing pores having a pore diameter larger than the kinetic diameter of the first gas and smaller than 1.5 times the kinetic diameter of the second gas;
- wherein the sensor element is configured so that the porous material adsorbs more of the first gas than of the second gas so that detection of the second gas by the sensor element is more sensitive as compared to detection of the first gas by the sensor element.

Embodiment 2

The sensor element of embodiment 1, wherein the pore diameter is in a range of about 4.6 Å to about 9 Å.

Embodiment 3

The sensor element of embodiment 1, wherein the pore diameter is in a range of about 5.1 Å to about 5.5 Å.

Embodiment 4

The sensor element of embodiment 1, wherein the semiconductor sensing material comprises a polycrystalline n-type semiconductor material doped with about 0.01% to 10% boron by weight, wherein the semiconductor material has an absorption edge of 600 nm or less, and the semiconductor material physically contacts both the first and second electrodes.

Embodiment 5

The sensor element of embodiment 1, 2, 3, or 4, wherein the first gas is acetone.

Embodiment 6

The sensor element of embodiment 1, 2, 3, 4, or 5, wherein the second gas is isoprene.

Embodiment 7

The sensor element of embodiment 1, 2, 3, 4, 5, or 6, wherein the sensor has a sensitivity ratio of the second gas to the first gas of at least 1.5.

Embodiment 8

The sensor element of embodiment 4, 5, 6, or 7, wherein the polycrystalline n-type semiconductor material comprises $WO_3$.

Embodiment 9

The sensor element of embodiment 8, wherein the $WO_3$ is doped with about 0.1% to about 0.3% by weight of boron.

Embodiment 10

The sensor element of embodiment 8, wherein the $WO_3$ is $\gamma$-$WO_3$.

Embodiment 11

The sensor element of embodiment 8, wherein the $WO_3$ is $\varepsilon$-$WO_3$.

Embodiment 12

The sensor element of embodiment 8, wherein the $WO_3$ is $\eta$-$WO_3$.

Embodiment 13

The sensor element of embodiment 1, 2, 3, 4, 5, 6, 7, 8, 9, 10, 11, or 12, wherein the porous material comprises a zeolite or a metal organic framework.

Embodiment 14

The sensor element of embodiment 13, wherein the zeolite comprises ZSM-5, ZSM-11, Zeolite Y, ZSM-12, beta zeolite, or Titano silicalite TS-1.

Embodiment 15

The sensor element of embodiment 14, wherein the zeolite comprises ZSM-5.

Embodiment 16

The sensor element of embodiment 14 or 15, wherein the Si/Al ratio of the zeolite material is in a range of 1 to 500.

Embodiment 17

A gas sensor comprising the sensor element of embodiment 1, 2, 3, 4, 5, 6, 7, 8, 9, 10, 11, 12, 13, 14, 15, or 16.

Embodiment 18

An isoprene sensor comprising the sensor element of embodiment 1, 2, 3, 4, 5, 6, 7, 8, 9, 10, 11, 12, 13, 14, 15, or 16.

Embodiment 19

A method of determining isoprene levels in mammalian breath comprising exposing the isoprene sensor of embodiment 18 to a breath of a mammal.

Embodiment 20

The method of embodiment 19, wherein the mammal is human.

Embodiment 21

A breath analyzing device comprising a container configured for reception of mammalian breath, and a sensor element of embodiment 1, 2, 3, 4, 5, 6, 7, 8, 9, 10, 11, 12, 13, 14, 15, or 16 disposed within the container and in physical contact with gas inside the container.

Embodiment 22

The breath analyzing device of embodiment 21, which is configured to selectively determine the content of isoprene in mammalian breath.

Embodiment 23

A medical diagnosis system comprising the isoprene sensor of embodiment 17 and a portion of a breath exhaled by a mammal.

EXAMPLES

Sensor Materials Development and Characterizations:

Example 1: Making Boron Doped Epsilon Phase $WO_3$

About 20 mg of boron doped tungsten oxide made as described in U.S. Provisional Patent Application 62/003,753 filed May 28, 2014, and U.S. Publication No. 2015/0346190 published Dec. 3, 2015, was mixed with 2 ml ethanol and sonicated for 60 mins. About 10 µl aliquots of the dispersion were dropped onto a sensor element (0.1×0.1 inch electrode, $Al_2O_3$ substrate, 10 mils thick, sensing electrode material is gold, electrode spacing 1 mils, finger width 4 mils, finger length 0.1 inch and with 3 electrode pairs, a pair of resistive Pt heating electrodes on the back of the substrate with resistance around 36 Ohm, P/N 614; Synkera Technologies, Colorado, USA). The sensor element was heated on a hot plate at about 140° C., and dried between each additional drop. Around 80 uL of the dispersion was used. The original drop coated sensors (S1 and S2) were then baked on under a full-spectrum Xenon lamp at 300 W output power, for about 60 minutes at about 120° C.

Example 2: Fabrication of Zeolite Modified Sensor

The sensor was fabricated following the same procedure in Example 1 was then further modified by the addition of a porous layer disposed upon the above described sensor material element. About 20 mg of zeolite material ZSM-5 (Si/Al ratio 26, ACS material, Medford, Mass.) was mixed with 2 ml ethanol and sonicated for 60 minutes. About 5 µl aliquots of the dispersion were dropped onto the original sensor as described in example 1. The sensor was heated on a hot plate at about 140° C., and dried between each additional drop. Around 40 uL dispersion was used. Then the zeolite modified sensor (S3-ZSM-5) was then baked on under a full-spectrum Xenon lamp at 300 W output power, for about 60 minutes at about 120° C.

Example 3: Fabrication of Zeolite Modified Sensor

In another embodiment, the original sensor was modified in the same way described in Example 2 except the zeolite material is replaced by Zeolite Y (S4-Y)

Example 4: Setup for Sensor Evaluation

The Sensor Element 1 (SE-1) constructed as described in the example above, was placed inside a test chamber having about 30 mL volume, with the gas inlet around 5 cm above the sensor surface. The sensing electrodes were connected to a multimeter (Tektronix DMM 4050, 6½ Digit Precision Multimeter, Tektronix, Inc., Beaverton, Oreg., USA), set to measure resistivity (ohms) under ambient atmospheric conditions and the heating electrodes were connected to a power supply at 5.8V and 0.161 A. The heating element generates heat that maintains an operating temperature at sensor surface, of about 380° C. The sensor was heated at this voltage in the ambient atmospheric environment for about 30 minutes and a stable resistivity baseline was achieved.

Stream of humid synthetic air [CAS 132259-10-0], Airgas, LLC, San Marcos, Calif., USA) having a relative humidity of about 90%, was generated by passing an 40° C. water bath at about 1.5 L/minute. 1 ppm acetone/air gas was generated by mixing 15 ppm acetone/synthetic air (Mesa Specialty Gases & Equipment, Long Beach, Calif., USA) with the humid synthetic air in 1:15 ratio and was then released into the container for varying amounts of time, e.g., 10 sec, about 8 sec, about 5 sec, and the change of resistance of the sensor element was recorded. The condition of this test gas was set to simulate human breath. After the injection of the acetone gas, the sensor was let recover to its original resistance in the ambient environment. 1 ppm isoprene/air gas was generated by mixing 100 ppm isoprene/synthetic air (Mesa Specialty Gases & Equipment, Long Beach, Calif., USA) with the humid synthetic air in 1:100 ratio and tested in the same manner.

The sensitivity to that gas is defined as the ratio of the minimum sensor resistance after exposed to the test gas ($R_{gas}$) to the baseline resistance at ambient environment ($R_{air}$), $S=R_{gas}/R_{air}$. The smaller the value, the greater sensitivity the sensor has.

Example 5: Sensor Evaluation for Acetone and Isoprene Sensitivity

The sensitivity of the unmodified sensor S1-2 and the corresponding zeolite ZSM-5 modified sensor S3 and zeolite Y modified sensor S4 to 0.5 ppm acetone and 0.5 ppm isoprene are shown in Table 4. It shows that without the zeolite coating the unmodified sensor is highly sensitive to both acetone and isoprene. As a result there is a lack of selectivity between these two gases, making accurate measurement of the concentration of either acetone or isoprene in a mixed gas sample, e.g., human breath, difficult. After the sensor is modified by the zeolite layer, it maintains the high sensitivity of isoprene, but decreases the sensitivity of acetone considerably. This can enable accurate measurement of isoprene alone in a mixture of acetone and isoprene gases or in human breath, thus providing a highly selective and sensitive isoprene sensor. S3 (ZSM-5 modified) shows better selectivity of isoprene to acetone, which is likely because the pore size of ZSM-5 is larger than the average diameter of acetone molecules and smaller than that of isoprene. As a result, isoprene cannot be adsorbed by ZSM-5. Zeolite Y reduces sensitivity to both acetone and isoprene. However, the reduction of sensitivity to acetone is greater. This may be because Zeolite's Y pore size is larger than the average diameter of acetone and isoprene, but since the acetone molecule is smaller it is more readily adsorbed by Zeolite Y.

TABLE 4

|  | 0.5 ppm acetone | 0.5 ppm isoprene |
|---|---|---|
| S1-unmodified | 0.494 | 0.496 |
| S3-ZSM-5 | 0.867 | 0.498 |
| S2-unmodified | 0.485 | 0.502 |
| S4-Y | 0.869 | 0.644 |

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the embodiments of the present disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments of the present disclosure and does not pose a limitation on the scope of any claim. No language in the specification should be construed as indicating any non-claimed element essential to the practice of the embodiments of the present disclosure.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the embodiments of the present disclosure. Of course, variations on these described embodiments will become apparent to those of ordinary skill in the art upon reading the foregoing description. The inventor expects skilled artisans to employ such variations as appropriate, and the inventors intend for the embodiments of the present disclosure to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A sensor element comprising: a semiconductor sensing material having an electroconductivity that is sensitive to the presence of a first gas and a second gas; and
a porous material containing pores having a pore diameter larger than the kinetic diameter of the first gas and smaller than 1.5 times the kinetic diameter of the second gas; wherein the sensor element is configured so that the porous material adsorbs more of the first gas than of the second gas so that detection of the second gas by the sensor element is more sensitive as compared to detection of the first gas by the sensor element, wherein the semiconductor sensing material comprises a polycrystalline n-type semiconductor material doped with 0.01% to 10% boron by weight.

2. The sensor element of claim 1, wherein the pore diameter is in a range of 4.6 Å to 9 Å.

3. The sensor element of claim 1, wherein the pore diameter is in a range of 5.1 Å to 5.5 Å.

4. The sensor element of claim 1 wherein the second gas is isoprene.

5. The sensor element of claim 1 wherein the sensor has a sensitivity ratio of the second gas to the first gas of at least 1.5.

6. The sensor element of claim 1 wherein the polycrystalline n-type semiconductor material comprises $WO_3$.

7. The sensor element of claim 6, wherein the $WO_3$ is doped with 0.1% to 0.3% by weight of boron.

8. The sensor element of claim 6, wherein the $WO_3$ is e-$WO_3$.

9. The sensor element of claim 1 wherein the porous material comprises a zeolite or a metal organic framework.

10. The sensor element of claim 9, wherein the zeolite comprises ZSM-5, ZSM-11, Zeolite Y, ZSM-12, beta zeolite, or Titano silicalite TS-1.

11. The sensor element of claim 9, wherein the zeolite comprises ZSM-5.

12. A gas sensor comprising the sensor element of claim 1.

13. An isoprene sensor comprising the sensor element of claim 1.

14. A method of determining isoprene levels in mammalian breath comprising exposing the isoprene sensor of claim 13 to a breath of a mammal.

15. The method of claim 14, wherein the mammal is human.

16. A breath analyzing device comprising a container configured for reception of mammalian breath, and the sensor element of claim 1 disposed within the container and in physical contact with gas inside the container.

17. The breath analyzing device of claim 16, which is configured to selectively determine the content of isoprene in mammalian breath.

18. A medical diagnosis system comprising the isoprene sensor of claim 13 and a portion of a breath exhaled by a mammal.

\* \* \* \* \*